US006254896B1

(12) United States Patent
Davis (10) Patent No.: US 6,254,896 B1
(45) Date of Patent: Jul. 3, 2001

(54) APPARATUS AND PROCESS FOR IN SITU MANUFACTURE OF ESSENCE FROM LIVING, UNCUT PLANTS

(76) Inventor: Brent W. Davis, P.O. Box 570, Lobelville, TN (US) 37097

(*) Notice: Subject to any disclaimer, the term of this patent is extended or adjusted under 35 U.S.C. 154(b) by 0 days.

(21) Appl. No.: 09/572,055

(22) Filed: May 17, 2000

(51) Int. Cl.$^7$ .................................................... A61K 35/78
(52) U.S. Cl. ............................................ 424/725; 47/58.1
(58) Field of Search ......................... 47/58.1; 424/195.1, 424/725

(56) References Cited

U.S. PATENT DOCUMENTS

| | | | |
|---|---|---|---|
| 3,928,584 | * 12/1975 | Hudson | 424/195.1 |
| 4,767,618 | 8/1988 | Grollier et al. | 424/74 |
| 4,839,168 | 6/1989 | Abe et al. | 424/74 |
| 6,013,524 | * 1/2000 | Friars et al. | 435/420 |

OTHER PUBLICATIONS

"The Twelve Healers And Other Remedies" by Edward Bach, Published by the C.W. Daniel Company Ltd., Essex, England, 1933, Revised 1952, Reprinted 1999.

"The Bach Flower Remedies Illustrations and Preparations" by Nora Weeks and Victor Bullen, Published by the C.W. Daniel Company Ltd., Essex, England, 1990.

* cited by examiner

Primary Examiner—Francisco Prats
Assistant Examiner—Kailash C. Srivastava
(74) Attorney, Agent, or Firm—Waddey & Patterson; Michael J. McCarthy; Richard S. Myers, Jr.

(57) ABSTRACT

The present invention relates to the in situ manufacture of plant extracts from living plants. Since the plant remains intact, a flower or other component of the plant can be extracted one or more times. Following the extraction process, the plant is typically able to continue with its lifecycle. Such extracts have a variety of uses including use for, but not limited to: herbal and homeopathic medicines, hair and skin treatments, and cosmetics. The present invention also relates to apparatus useful for manufacturing plant extracts from living plants.

11 Claims, 3 Drawing Sheets

APPARATUS AND PROCESS FOR IN SITU MANUFACTURE OF ESSENCE FROM LIVING, UNCUT PLANTS

BACKGROUND OF THE INVENTION

1. Field of the Invention

The present invention relates generally to devices and methods for making plant extracts. More particularly, this invention pertains to an apparatus and process for manufacture of a plant extract useful in homeopathic medicine, hair and skin treatments, and cosmetics and perfumes.

2. State of the Prior Art

Dr. Edward Bach was a medical physician who developed a group of healing flower and herb essences between the years 1928 and 1935. He administered these plant essences to produce subtle but powerful benevolent forces which raised the "vibrational frequency" of an ill person to a higher level; thus, enhancing the natural resistance to overcome the lower "vibrational frequencies" associated with disease.

Bach extracted plants using historical methods by making either a sun infusion of cut flowers or buds in water or by boiling cut flowers or buds (a decoction). However, specific extraction techniques (e.g., great attention to not touching the cut flowers or the extract they make), and formulation into a high dilution of the plant extract to achieve homeopathic type effects have become regarded as distinctly his. The Bach method of producing flower remedies has been adopted internationally, and is in use commercially by approximately sixty companies worldwide. Bach flower remedies have over the counter (OTC) drug status in the United States since they are included in the U.S. homeopathic pharmacopoeia. They are also officially recognized in the homeopathic pharmacopoeias of many other developed countries. Bach's Sun Infusion Method for extracting flowers A thin, plain glass or crystal bowl (about one-half pint capacity, not cut glass or oven glass), a jug (glass or china), and a one ounce dropper bottle should be sterilized by placing them in cold water in a saucepan which is brought to a boil, boiled for twenty minutes, cooled, and then dried carefully. The bowl and jug are wrapped in a clean cloth. When cooled, the one ounce bottle is filled about halfway with brandy, capped, and labeled with the name of the extraction to be prepared and the word "Tincture".

A field or hilltop where the plants, trees or bushes are growing, is pre-selected for the extraction procedure which is carried out on a cloudless sunny morning. Before 9 a.m., the bowl is placed on the ground near the flowering plants, away from any tall plants or structure which might cast a shadow over the bowl as the sun travels across the sky. The bowl is filled to the brim with water from a nearby clear pure stream, or from a bottle, sterilized as described above, and filled with spring or mineral water which is carried to the site.

A broad leaf is placed on the palm of the hand and then the flower heads or the flowering spikes, are picked or cut from as many plants or bushes of the same kind as possible. The flower heads are picked just below the calyx, or flowering spikes. The picked or cut flowers are quickly floated on the surface of the water in the bowl. This process is repeated until the whole surface of the water is thickly covered, with overlapping flowers, but wherein each flower touches the water. During this process, casting a shadow over the bowl and touching the water with the fingers is avoided.

The bowl is left in full sunshine for three hours. At the end of this time and with a stalk from the plant being extracted, the flowers are removed. Again, touching the water with the fingers is avoided. The now vitalized water is poured into the jug and into the remaining half of the labeled dropper bottle containing the brandy which now constitutes the Tincture. If the Tincture is kept for several years, a slight sediment may form at the bottom of the bottle, this is not harmful. The liquid can be filtered into another sterilized bottle and labeled with a duplicate label.

The Tincture will retain its strength indefinitely, and is the one from which stock bottles are prepared. The stock bottle is the second stage in the preparation of the remedy and it is from this that the treatment bottle is made up. To prepare a stock bottle, a sterilized one ounce dropper bottle is filled with brandy. Two drops from the Tincture bottle of the remedy are placed into the stock bottle. The cap is fastened securely and the bottle is labeled with the name of the remedy and "stock".

The treatment bottle is the third stage in the preparation and it is from this that the required daily doses are taken. After deciding which remedy or combination of remedies are required, two drops from each remedy stock bottle are placed into a sterilized one ounce dropper bottle (the treatment bottle). The remainder of the bottle is filled with pure spring or mineral water (available in bottles from most supermarkets or health stores), and a teaspoon of brandy is added to help preserve the water if it is likely to be subjected to a warm environment. The cap is fastened securely and the bottle is labeled with the name(s) of the remedy(s) and "treatment".

Cut Flower Extractions as Conditioners and Cosmetic Additives

Extractions of numerous cut flowers and ground plants are commonly utilized as conditioners and additives, such as for hair treatments including shampoos, hair conditioners, gels, etc. and in cosmetics, such as for the face, eyes, hands, feet, and other areas. For instance, U.S. Pat. No. 4,767,618 to Grollier et al. describes utilization of cut flowers and ground plant extracts for these purposes. In particular, this patent pays close attention to making sure that the flower or plant part is pulverized until a granulometry lower than 125 microns is obtained. Additional shampoo preparation with extracts of birch and rosemary are described in U.S. Pat. No. 4,839,168 to Abe et al., incorporated herein by reference. This shampoo is described to impart good hair style retention and good feeling of touch.

However, homeopathic physicians, their patients, and numerous other people desire flower and plant extracts that are manufactured according to less extreme conditions. The Sun Extraction Method developed by Bach and generally described above, is one such method, but the inventor has discovered a method and an apparatus for an even less destructive method for manufacturing a plant extract.

SUMMARY OF THE INVENTION

The present invention includes an apparatus and a method for manufacture of flower and plant extracts wherein the extract is manufactured in situ from living, uncut plants. The apparatus and method can be used on any above ground component of any living plant including, but not limited to: blooms, buds, leaves, stalks, seeds, berries, and aerial roots. Damage to extracts manufactured as described in the present invention is kept to a minimum and the potency of each extract is maximized. Without being bound by mechanism or theory, in certain embodiments, the extract manufactured as described in the present invention includes a vital energy of the plant. This vital energy is obtained in a more potent form (and in certain embodiments, a virtually optimal therapeutically potent form) than heretofore due to the fact that the plant is living and uncut while the vital energy is being extracted from the plant. The inventor hence posits that the plant transmits a greater potency to the extracting medium than could be achieved by the Bach and similar methods in which the flower or bud is cut off from the mother plant.

An object of the present invention is to manufacture an extract of a flower, or other component of any living plant, with minimal damage to the extract, and in certain embodiments, with minimal disruption of a vital energy being transmitted to the extract. It is preferred that minimal damage is done to the flower or plant and that the plant can continue its natural lifecycle while being extracted. Another object of the present invention is to provide an apparatus designed to collect an extract of a flower, or other component of any living plant, with minimal damage to the extract, and preferably the flower or other plant component being extracted, and in certain embodiments, with minimal disruption of a vital energy being transmitted to an extract solution. Still another object of the present invention is to provide a kit for collecting an extract of a flower, or other component of any plant, with minimal damage to the extract and preferably without damaging the flower or other component.

Accordingly, the present invention describes methods whereby a flower, or other above ground component of any plant, is extracted while the flower or other component is living, fully intact, and attached to the living plant. It is preferred that the living plant is not uprooted and it should not be uprooted during the extraction process. In certain embodiments, at least a portion of the flower or other component of the living plant is contacted by an extraction solution for a period of time. The plant essence is taken up by the extraction solution.

The present invention also describes an apparatus for holding the extraction solution proximate to the flower, or other component of the plant, during the extraction process. In certain embodiments, the apparatus comprises a vessel having a bowl shaped chamber for holding the extraction solution proximate to the plant component. In certain embodiments, the apparatus comprises a vessel having a substantially U-shaped bottom; an opening above the U-shaped bottom; a chamber wall having an inner chamber wall, an outer chamber wall, and a chamber wall edge; and a slot in the chamber wall extending from a point on the chamber wall edge to an interior point on the chamber wall.

In certain preferred embodiments of the present invention, a method of extraction is described wherein a stem of a plant is passed through the slot in the extraction vessel, the vessel is positioned such that when the extraction solution is added it contacts the component of the plant for which extraction is desired, the slot is sealed by any method that generates a watertight seal including around the stem of the plant, and the extraction solution is added to the desired level. A highly preferred sealant is beeswax.

DESCRIPTION OF THE PREFERRED EMBODIMENTS

The present invention includes methods for extracting flowers, and other components of plants, wherein the flowers and plants are in their natural living state. The present invention further includes an extraction apparatus specifically and uniquely designed for such extraction. The embodiments of the present invention are less invasive and minimize damage to the plant during the extraction process. With regard to the plant and the plant component, preferred embodiments of the present invention do not involve the killing, grinding, pulverizing, severing, cutting, crushing, plucking, or other such steps which are found in known methods for manufacturing a plant extract. In preferred embodiments, the plant, including the component from which the extraction is made, is left to complete its lifecycle, essentially undisturbed. Thus, it is also preferred that the connection between the plant and its natural surroundings, e.g. the earth, remains intact.

The essence of the plant which is imparted to the extraction solution can be in any form as the present invention is not bound to mechanism or theory. For example, the essence may be plant molecules or plant chemicals. The essence may be what is known as plant energies including vibrational energies, also.

Without being held to mechanism or theory, it is believed by the inventor that the present invention enhances the vital energy and vibrational energy that the plant or plant component transmits to the extracting solution. Also without being held to mechanism or theory, the present invention yields a plant extract that is natural and pristine yielding advantages in potency and quality especially with regard to use in homeopathic medicine, but also, as an additive to hair treatments (e.g., shampoos, conditioners, gels, setting sprays, etc.), skin conditioners (e.g., hand lotion, foot cream, body lotion, face lotion), and cosmetics (e.g., face and eye cosmetics).

Homeopathy

In the healthy condition of man, the spiritual vital force, the dynamis that animates the material body, rules with unbounded sway, and retains all parts of the organism in admirable, harmonious, vital operation, as regards both sensations and functions, so that our indwelling reason-gifted mind can freely employ this living, healthy instrument for the higher purposes of our existence. (founder of homeopathy, Samuel Hahnemann Organon)

The essential laws of homeopathy:

1) Health is from an unhampered and balanced expression of energy.
2) Imbalance is caused by a defective action of the defense mechanism.
3) Imbalance is a blockage or distortion of energy in the body, and may be caused by shock, injury, fright, bad news, etc., or from wrong thinking or abusive habits.

The homeopathic practitioner typically treats disease in man by generally applying the following principles, although this invention is not bound by mechanism or theory in any way. Disease is destroyed in a permanent manner by another more powerful force that bears a strong resemblance in its mode of manifestation. Those substances in a gross material form that when administered to a healthy test subject produce pathogenic symptoms will cure those same symptoms when they are a disease manifestation in an ill subject if administered in a diluted and dynamized form. Thus, medicines must be dynamized and potentized (highly diluted) in order to affect the vital energy bodies (represented in FIG. 3). (see, for example, The Original Writings of Edward Bach, C. W. Daniel Co., Essex, England (1990) incorporated herein by reference.) In general, the homeopathic practitioner follows the law of minimum dose. That is, the dose should be given in the smallest amount necessary to induce a vital reaction that will dislodge and throw off the aberrant frequency of disease.

The Vibrational Medicine Paradigm

Institutional Western medicine has been described as treating the human body quite like a machine composed of interrelated tissues and organs, powered by cellular reactions, and controlled by electrochemical impulses in the brain and central nervous system. The influence on human physiology of Spirit, Divine Creative Intelligence, and other metaphysical forces is disallowed in its paradigm.

Ancient Egyptian, Arabic, East Indian, Oriental, and Aboriginal medical systems worldwide, as well as homeopathic medicine, on the other hand, are considered to take a philosophical and very much expanded view of how the body operates, and of the forces that animate it. Over millennia, observant healers and physicians noticed that tiny doses of therapeutic substance could produce profound therapeutic changes in the human body even though the doses were so diluted that the analytical processes of the practitioner found no detectable material substance. Such therapeutic changes were explained in the context of a multi-dimensional and metaphysical view of the human body (see e.g., Vibrational Medicine (1988), Richard Gerber, M.D., Bear and Co., Santa Fe, New Mexico, incorporated herein by reference).

Figure 3:
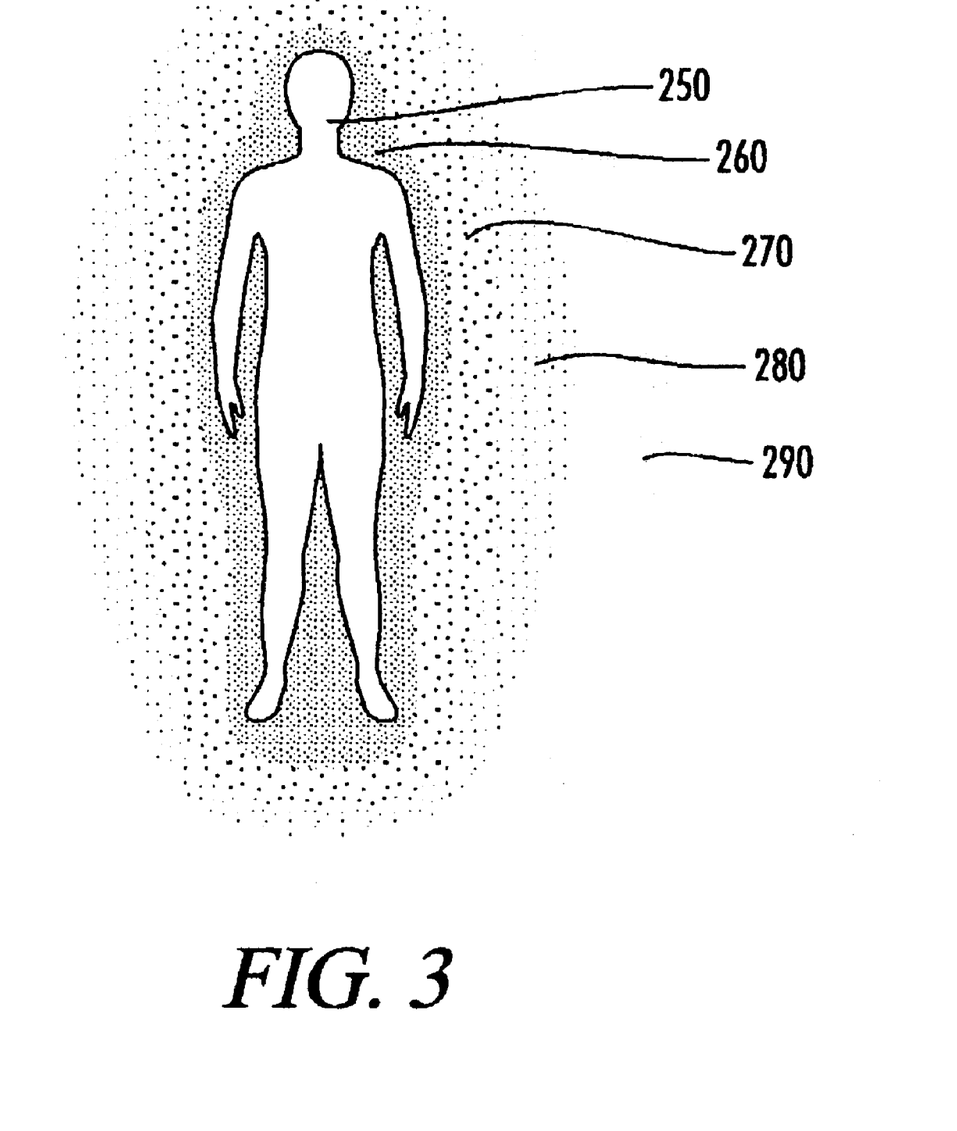
FIG. 3 is an illustration of certain vibrational shells known to homeopathic medicine. Shown in the illustration are representations of the physical body 250, the electric body of acupuncture (Shell #1) 260, the emotional/soul body (Shell #2) 270, the spirit/mind (Shell #3) 280, the god-linked shell (Shell #4) 290.

According to a composite view derived from ancient medical systems and contemporary vibrational medicine (practiced in homeopathic medicine), FIG. 3 depicts the several layers that comprise the full human being. Again, without the present invention being bound to mechanism or theory, it is posited that the outermost shells essentially influence and determine the balance (state of health) of the inner shells. Each successive shell going outward from the physical body is believed to resonate at a higher frequency, possessing a more subtle character, than the shell inside it, yet exerting a greater power of influence over the state of the physical body. For example, if an individual is suffering from very stubborn, imbalanced emotional states (shell 2, see FIG. 3, 270), it is believed that it may lead to strong imbalances in the electrical acupuncture meridians (shell 1, 260) and reflect into the physical body 250 causing disease symptoms. If this individual were treated with the appropriate, high frequency flower remedy for his condition (which acts strongly on shells 1 and 2), and consciously employed his spiritual will for reparation and transformation (shell 3, 280), he might well be restored to health. This model is consistent with the teachings of Dr. Bach and many flower remedy practitioners generally subscribe to this model.

Additional theory (not binding upon the present invention) from materials sciences physicist William Tiller, Ph.D. of Stanford University, is as follows:

Man appears as a being whose primary level of existence is at the non-space, non-time levels of the Universe, and who has placed himself in a space-time vehicle of consciousness for the purpose of growing in awareness of the True Self and of generating coherence in the True Self. Our perception mechanisms at the space-time vehicle level lock us into a narrowly restricted view of reality and the Self. Disharmony created by the ego at the deeper level of self, materializes as error or disease in the space-time vehicle as an indicator that error has been created at a primary level.

Self-healing or healing by another involves energy coordination at a variety of levels and teaches us that the sensory apparatus of the space-time vehicle perceives only the "World of Appearances" and has no knowledge of Reality. It teaches us that the space-time vehicle is not Life but only a simulator of life whose only role is as a teaching tool. With our thoughts and attitudes, we continuously reprogram the simulator from the Mind level of the multidimensional universe and continuously generate our individual and collective futures by such behavior. Source: W. Tiller, "Theoretical Modeling on the Function of Man," in Healers and the Healing Process, ed. G. Meek (Wheaton, Ill.: Theosophical Publishing House, 1977), incorporated herein by reference.

Teachings of Dr. Bach and the Use of Flower Remedies

In the booklet Heal Thyself, Dr. Bach describes his views, which are highly regarded by this inventor and many other holistically oriented practitioners, regarding principles and precepts that influence the domain of healing in which flower remedies act. (Heal Thyself, in The Bach Flower Remedies, Keats Publishing, Inc., New Canaan, Conn. (1997) incorporated herein by reference). The following are illustrative excerpts from Heal Thyself:

... [A] great principle is the understanding of the Unity of all things: that the Creator of all things is Love, and that everything of which we are conscious is in all its infinite number of forms a manifestation of that Love, whether it be a planet or a pebble, a star or a dewdrop, man or the lowliest form of life.

... There are two great errors: first, to fail to honor the dictates of our Soul, and second, to act against Unity.

... If we have in our nature sufficient love of all things, then we can do no harm; because that love would stay our hand at any action, our mind at any thought which might hurt another . . . . The real primary diseases of man are [those] found to be adverse to Unity.

[Heal Thyself Chapter 3]

... The ultimate conquest of all will be through love and gentleness, and when we have sufficiently developed those two qualities nothing will be able to assail us, since we shall ever have compassion and not offer resistance; for . . . it is resistance which damages. [Heal Thyself, Chapter 4]

... the real victories of life come through love and gentleness, . . . no force whatever must be used. [Heal Thyself, Chapter 5]

The present invention was inspired by these and other teachings of Dr. Bach. However, the inventor is the first to conceive of the idea that a flower extract (or extract of any other component of a plant), essence, and energy can be manufactured or harvested in situ in an extraction vessel without cutting, picking, or otherwise severing any part of the plant especially the component to be extracted and the first to describe methods and apparatus thereof. While not being bound to mechanism or theory, it is believed that the non-destructive nature of the manufacturing process yields essences and extracts particularly useful for herbal and homeopathic medicine and useful as additives in hair and body treatments, and cosmetics as described herein.

A method for in situ Manufacture of Essence from Living, Uncut Plants

Certain embodiments of the present invention describe a method for collecting an extract of a living plant, comprising: selecting the living plant; placing an extraction vessel proximate to a component of the living plant; adding an amount of an extraction solution to the extraction vessel; and contacting the extraction solution to the component of the living plant, wherein the component of the plant remains attached to the living plant.

The order of steps is not believed to be important (e.g., the extraction solution may be added before the vessel is positioned or after). Any plant or plant component known wherein at least a portion of the plant lives at least part of its lifecycle above ground, can be extracted by the methods of the present invention. A number of specific plants are listed in Table 1 (see the Examples section); however, this list is not meant to limit the scope of the present invention. Also, any component of a plant can be extracted so long as the component lives above ground, at least temporarily. It is important that the plant is not killed during the extraction process and that the component of the plant is not severed from the plant. The terms "extraction vessel", "extraction cup", and "extraction bowl" are used interchangeably herein.

In certain embodiments, the component is an aerial root or a berry. In certain preferred embodiments, the component is a seed (including a developing seed, groups of seeds, mature seeds still attached to the plant, etc.). In certain more preferred embodiments, the component is a leaf or a stalk including a blooming stalk. In certain still more preferred embodiments, the component is a bud of the plant (including a developing bud, a bud that is about to open into a flower, etc.). In certain highly preferred embodiments, the component is a flower (including a bloom, a soon to open flower, a fully opened flower, a fading flower still attached to the plant, a flower stalk, a blossom, etc.).

It is believed that the extraction vessel can made from any material able to hold water. In certain embodiments, the extraction vessel itself, or a fluid holding chamber within the extraction vessel, is comprised of plastic. Construction with plastic is particularly useful in harsh environments wherein extremes of temperature and precipitation (e.g., hail) may excessively damage other materials. In certain embodiments, the extraction vessel itself, or a fluid holding chamber within the extraction vessel, is comprised of blown glass. Construction with blown glass is particularly useful in harsh environments, where extremes of temperature or sun may damage other materials.

In preferred embodiments, the extraction vessel is comprised of wax and more preferably beeswax. Beeswax is an ideal natural material for construction of the extraction vessel or parts thereof, such as a chamber within the extraction vessel for holding the extraction solution. However, additional waxes such as paraffin may be substituted for beeswax in certain embodiments.

A highly preferred extraction solution is a sample of water taken from a stream or spring near to where the plants being extracting are growing. It is highly preferred that the stream is a flowing, unpolluted, clear stream. In certain embodiments, a sample of water from another suitable stream or commercially available mineral or spring water is used. Alternatively, the extraction solution may be any other liquid known to be used in the manufacture of plant extracts.

The essence or extract is harvested or manufactured by contacting the component of the living plant to the extraction solution for a period of time without severing the plant or the component of the plant. In certain embodiments (see FIG. 1, for example), where the component is perched upon a stem of the plant, the stem is passed through a slot in an extraction cup (or extraction vessel), the extraction cup is positioned proximate to the component (preferably such that the lip of the extraction cup is above at least a lower portion of the component), the slot is sealed watertight, and extraction solution is added to the extraction cup such that the extraction solution contacts the component. In certain embodiments, the slot is sealed by placing an adequate portion of wax, preferably beeswax, up to and preferably overlapping the plant stem and the edges of the slot in the extraction vessel. The wax can be heated (e.g., by a burnishing tool that has been placed into a heat source) by a heat source (e.g., a lighter or propane torch) so that it forms a seal with the plant stem and the extraction vessel. An amount of wax, or other sealant, can be painted onto the area of the plant stem and the edges of the slot in the extraction vessel to complete the seal and to make the seal watertight. In certain embodiments, it is preferred that the sealant, especially a wax sealant, is heated with a heat source to warm it or to melt it for painting into the seal. Certain sealants may be pliable or liquid enough for placing into the seal at ambient temperature.

Figure 2:
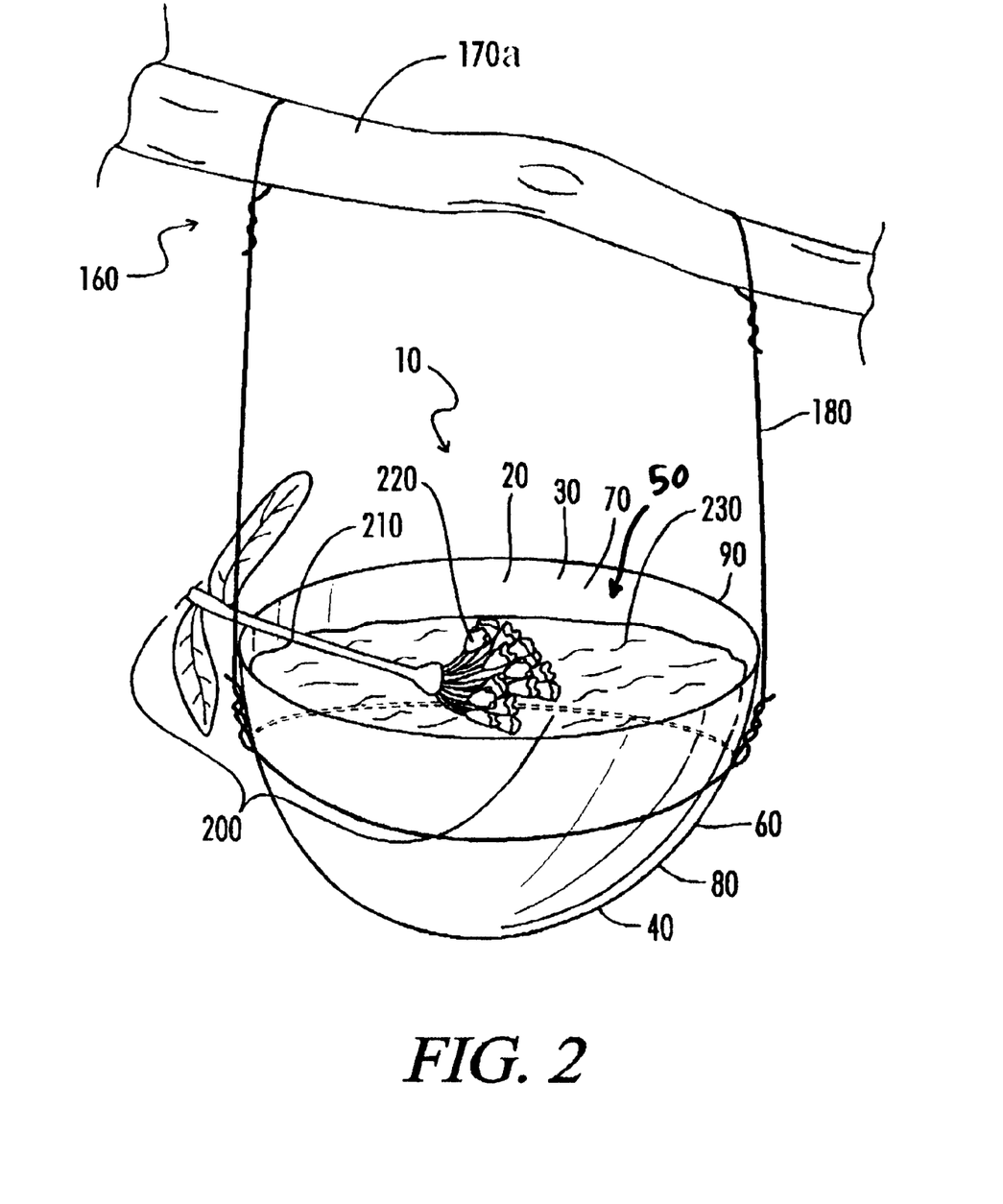
FIG. 2 is an illustration showing another embodiment of an extraction apparatus for in situ manufacture of a plant essence from a living, uncut plant component.

In certain other embodiments, an extraction cup is placed proximate to a component of a plant wherein the component is hanging down (see FIG. 2, for example). An amount of extraction solution is added to the extraction cup to contact the component for a period of time.

The amount of time that the extraction solution is contacted to the component of the plant is generally determined by the flower remedy technician who may be a practitioner or lay person. A preferred period of time for extraction is approximately 3 hours. Alternatively, the period of time for extraction may be less than 3 hours. In certain embodiments, the period of time for extraction is more than 3 hours. In certain preferred embodiments, the period of time for extraction is from approximately 3 hours to approximately 24 hours. In certain preferred embodiments, the period of time for extraction is from approximately 24 hours to approximately 3 weeks. The extraction is typically performed under the natural environmental conditions (temperature, humidity, sunlight, shade, precipitation, etc.) in which the plant is living.

In general, the length time for exposure of the plant part to the extraction medium depends first on the structural characteristics of the part. If, for example, a flower bud is very delicate or friable, it generally does not need to extract more than 3 hours, and may be better to have the extraction medium removed from the extraction vessel by pipette sooner than 3 hours to assure that wilting of the plant part does not occur. A tough skinned developing seed, on the other hand, might require several changes of extracting medium over days or weeks as it undergoes development and maturation. Very brief exposure of a plant part to the extracting medium would be required if it were to be extracted under the influence of a rapidly changing celestial configuration, such as a solar or lunar eclipse (for e.g., the length of the event or approximately thereabout).

After the essence or extract is manufactured, the solution may be diluted in certain embodiments. In general, extracts of the present invention may be diluted as described below. The extracting medium in which the plant part is resting is called the mother tincture or essence. It is collected, filtered, then preserved with approximately an equal part of pure grain alcohol, bringing the alcohol percentage to between approximately 40% to approximately 50%. The first dilution is the stock dilution and is prepared, in general, by adding approximately two to approximately ten drops of the mother tincture into approximately one quart of clean water and typically preserved with ethanol (e.g., so that it is 20% alcohol to prevent spoilage). The final dosage bottle dilution is typically prepared by adding approximately 4 drops of the stock dilution to an approximately one ounce bottle of approximately 20% alcohol in water. The consumer generally places approximately 4 drops from the dosage bottle into a consumable medium (e.g., ¼ glass clear or filtered water) to create the dose.

In certain highly preferred embodiments (see for example, FIG. 1), an extraction vessel 20 is provided for collecting an extract of a living plant 200, comprising: a chamber 30 having a substantially U-shaped bottom 40; a chamber wall 60 having an inner chamber wall 70, an outer chamber wall 80, and a chamber wall edge 90; and a slot 100 in the chamber wall 60 extending from a point on the chamber wall edge 110 to an interior point on the chamber wall 120. It is preferred that there is an opening 50 above the U-shaped bottom. The extraction apparatus 10 may be supported by a support apparatus 160. In certain preferred embodiments, the chamber 30 is comprised of wax and more preferably of beeswax. Alternatively, the chamber may be comprised of blown glass or plastic or another material that holds water. In certain preferred embodiments, an extraction apparatus 10 includes an extraction vessel 20 and a support apparatus 160. In certain preferred embodiments, the extraction vessel 20 further comprises a seal 130 in the slot 100 in the chamber wall 60 formed with a sealant 140. It is preferred that the seal 130 is water tight for holding an extraction solution 230 which is preferably water.

Figure 1:
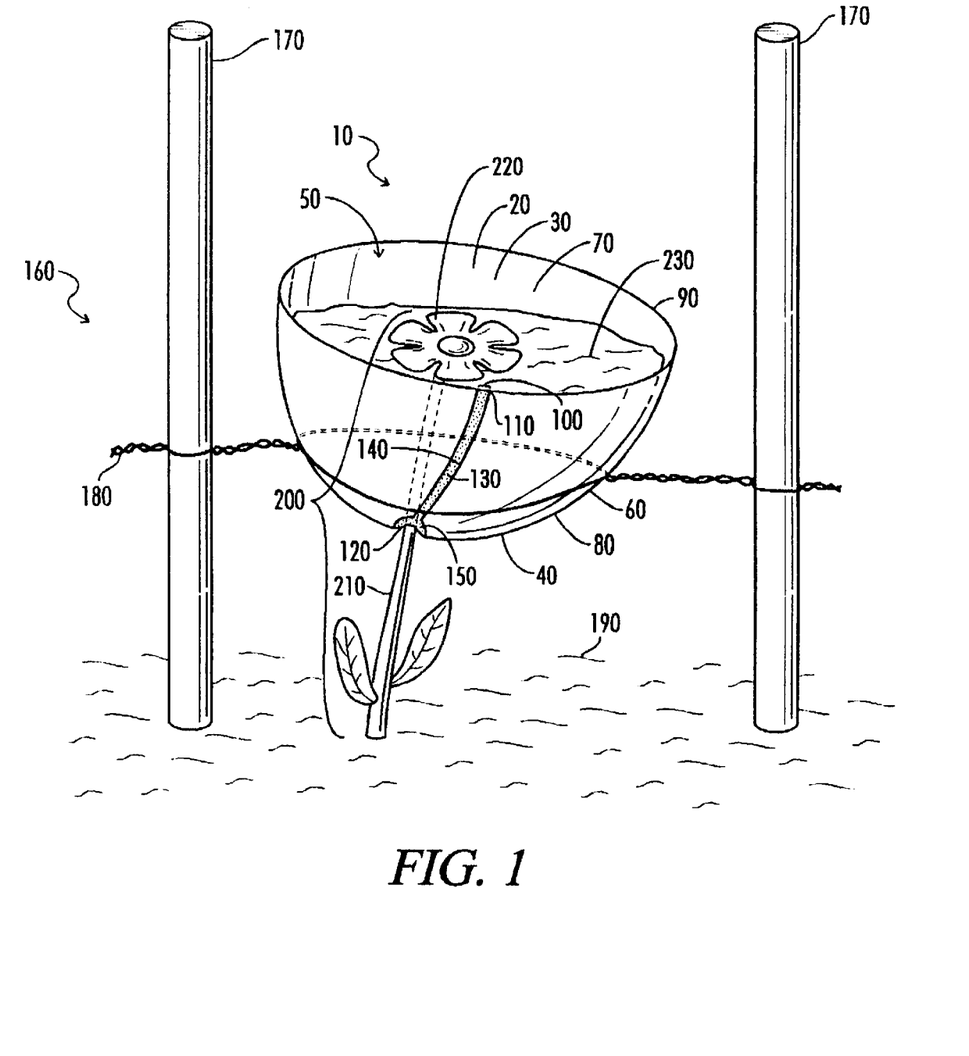
FIG. 1 is an illustration showing an embodiment of an extraction apparatus for in situ manufacture of a plant essence from a living, uncut plant component.

In other preferred embodiments (see for example, FIG. 1), an extraction apparatus is provided for collecting an extract of a living plant, comprising a chamber 30 having a substantially U-shaped bottom 40, an opening above the U-shaped bottom 50; a chamber wall 60 having an inner chamber wall 70, an outer chamber wall 80, and a chamber wall edge 90; a slot 100 in the chamber wall 60 extending from a point on the chamber wall edge 110 to an interior point on the chamber wall 120; a stem 210 of the living plant 200 extending through the slot 100, optionally proximate to the interior point on the chamber wall 120; and a component of the living plant 220 attached to the stem of the living plant 210. It is preferred that the living plant remain rooted in the ground and never, crushed, cut, plucked, ground, or severed. It is preferred that the plant and the plant component remain essentially intact. It is also preferred that the chamber 30 is comprised of beeswax; however, blown glass, plastic, or other materials may be used, alternatively. In certain embodiments, the extraction vessel 20 may be supported by a support apparatus 160. One embodiment of a support apparatus 160 is shown in FIG. 1. This support apparatus 160 includes one or more support stakes 170 and one or more support wires 180, wherein the stakes are driven into the ground and the wires are fastened to the stakes 170 and positioned proximate to the extraction vessel 20 for holding the extraction vessel 20 proximate to the component 220 of the living plant 200. In certain preferred embodiments, the extraction vessel 20 further includes a seal 130 comprised of a sealant 140. It is preferred that the sealant 140 forms a water tight seal 130 in the slot 100 in the chamber wall 60. It is also preferred that a water tight seal is formed around the stem of the living plant 150.

In another embodiment of the present invention (see for example FIG. 2), the extraction vessel 20 comprises a chamber 30 having a substantially U-shaped bottom 40, an opening 50 above the U-shaped bottom, a chamber wall 60, an inner chamber wall 70, and outer chamber 80, a chamber wall edge 90, and a support apparatus 160. Another embodiment of a support apparatus is shown in FIG. 2 and may include one or more support wires 180 fixed to a rigid structure. In the embodiment shown in FIG. 2, the rigid support structure comprises a tree branch 170a. The support structure can be any means for holding the extraction vessel proximate to the component 220 of the living plant 200 to be extracted. For example, the vessel 20 may be supported by one or more rocks, forms made or any partially rigid material (such as closed cell foam or blown molded plastic or foam), bags filled with fluid, books, the earth itself (especially for short plants or plants with a component near the earth), any solid object, and any semisolid object.

The present invention also provides a kit for collecting an extract of a living plant, comprising: an extraction vessel and a set of instructions describing a method for collecting an extract of the living plant, wherein the living plant remains rooted and wherein the living plant remains intact. In certain preferred embodiments of the kit, the extraction vessel is comprised of beeswax. Alternatively, the extraction vessel can be made of blown glass or plastic. In certain preferred embodiments, the kit further comprises an amount of water in a suitable container. It is preferred that the water is derived from a clear, flowing, unpolluted stream or spring. However, the water may also be derived from commercially available mineral water or spring water.

In another embodiment of the present invention, a kit is provided for collecting an extract of a living plant, comprising: an extraction vessel having a slot in a wall of the extraction vessel; a sealant; and a set of instructions describing a method for collecting an extract of a living plant wherein the living plant remains rooted and wherein the living plant remains intact. It is preferred that the extraction vessel is comprised of wax and more preferably beeswax. Alternatively, it may be comprised of blown glass, plastic, or other material that is waterproof or water resistant. It is further preferred that the sealant be comprised of wax and more preferably beeswax. In certain embodiments, the kit further comprises a heat source. In certain embodiments, the kit further comprises an amount of water in a suitable container. Again, it is preferred that the water is derived from a clear, flowing, unpolluted stream or spring. However, the water may alternatively be derived from commercially available bottled mineral or spring water.

A kit of the present invention may further comprise any embodiment or part described in the present invention. In addition, a kit may further comprise a container for holding items incorporated in the kit. In certain embodiments, the container may be any means for holding objects. For example the container may be, but is not limited to: a bag, a box, a plastic box, a wood box, and a metal box. In embodiments where the container is a box, the box is preferred to include a bottom, more than two sides, and a lid wherein the lid can be opened. The container may be formed to conform to a desired shape or volume and may contain packaging material for maintaining items of the kit in an orderly fashion (for example, foam with cutouts shaped to hold kit components).

EXAMPLE 1

An example of a preferred embodiment describing a method for in situ flower essence manufacture from living (uncut) plants is described herein.

A freshly opened flower is chosen for extraction. An extraction cup made of beeswax is mounted proximate to the flower with the stem of the flower passed through a slot in the extraction cup (see, for example, FIG. 1). The extraction cup is seated on substantially stiff wires running under the extraction cup and fastened to support posts (dowels) anchored into the ground.

A beeswax sealing strip is positioned so that it touches the stem at the center of the extraction cup and overlaps each side of the stem slit (slot). The sealing strip is pressed into place with the fingers, avoiding touching the plant part being extracted. A burnishing tool is heated with a propane torch flame and pressed into the beeswax sealing strip and the edges of the slot of the chamber of the extraction vessel merging the beeswax and forming a seal. An amount of beeswax is heated in a stainless steel cup with the propane torch until substantially melted. The heated beeswax is painted into any gaps in the seal of the slot with an artist paintbrush. The beeswax cools and forms a watertight seal around the flower stem and the extraction vessel. Thus, the sealant fills the slot in the extraction cup to form a watertight seal in the extraction cup including around the stem of the plant which penetrates the wall of the extraction vessel chamber.

The extraction cup is filled with pure water from a clear running stream in the flower until the water is contacting the underside of the flower for a period of three hours. Then the water is removed into a brown glass container with lid with a clean glass pipette and bulb. Sufficient grain alcohol is added to bring the plant extract (mother tincture) to approximately 40% alcohol for purposes of preservation and stabilization (thus, it is believed that the accuracy of the percent alcohol is not critical). When the extraction is finished, the extraction cup is removed from the flower allowing it to proceed to the next stage in its lifecycle. (If the flower is friable, the cup is left in place, for a time, as removing it may destroy the seed head.) The wax cup is recycled.

EXAMPLE 2

Before the extraction cup is removed from the flower in Example 1, a fresh aliquot of water is added to the extraction chamber and the flower is extracted a second time. This is possible because the flower is not damaged by the extraction process.

EXAMPLE 3

Example 1 is repeated more than two times (before removing the extraction vessel) such that multiple samples of flower extract are collected from one mounting of the extraction vessel.

EXAMPLE 4

Examples 1, 2, and 3 are repeated with a plant bud.

EXAMPLE 5

Examples 1, 2, and 3 are repeated with a plant bud that opens during the period of time for the extraction (in this case 3 or more hours).

EXAMPLE 6

Examples 1, 2, and 3 are repeated with a group of seeds on the living plant.

EXAMPLE 7

Examples 1, 2, and 3 are repeated with a group of berries on the living plant.

EXAMPLE 8

Examples 1, 2, and 3 are repeated wherein the component of the plant is a leaf of the living plant.

EXAMPLE 9

Examples 1, 2, and 3 are repeated wherein the component of the plant is a stalk of the living plant.

EXAMPLE 10

Examples 1 through 9 are repeated except that the component of the plant is pendulous (it hangs downward, see, for example, FIG. 2) and the chamber of the extraction vessel does not have a slot.

EXAMPLE 11

Examples 1 through 10 are repeated with a plant that is growing in the sun.

EXAMPLE 12

Examples 1 through 10 are repeated with a plant that is growing predominantly in the shade.

EXAMPLE 13

Examples 1 through 10 are repeated with a plant that is growing indoors.

EXAMPLE 14

Methods for in situ manufacture of an essence from a living plant, as disclosed herein are used to extract components of each plant that is described in the Homoeopathic Pharmacopoeia, Eighth Edition, Volumes I and II, (1979) American Institute of Homeopathy (Publishers), Falls Church, Virginia, incorporated herein by reference.

EXAMPLE 15

Methods for in situ manufacture of an essence from a living plant, as disclosed herein are used to extract components of each plant that is described in The Twelve Healers by Edward Bach (1933, reprinted with revisions 1999) C. W. Daniel Company Ltd., Essex, UK, incorporated herein by reference).

EXAMPLE 16

Examples 1 to 9, or 10, and 11, 12, and 13 are repeated for each of the plants listed below in Table 1. It should be noted that Table 1 lists preferred plants, but is not meant to limit the scope of the present invention as many additional plants and plant components are useful.

TABLE 1

| PREFERRED PLANTS | | |
| --- | --- | --- |
| Asclepias tuberosa | Astragalus | Blue-eyed grass |
| Agrimony | Basil | Blue Flag |
| Alfalfa | Beech | Boldo |
| Angelica | Beth Root (Trillium | Boneset |
| Apricot | species) | Buchu |
| Arnica | Bidens | Burdock |
| Artemisia | Black Cohosh | Calendula |
| Arum species | Black Walnut | California Poppy |
| Aspens | Blood Root | Cassia |
| Catnip | Ginseng | Oregon Grape Root |
| Cayenne | Golden Rod | Osha |

TABLE 1-continued

PREFERRED PLANTS

| | | |
|---|---|---|
| Centaury | Goldenseal | Passion Flower |
| Cherry Bark | Gotu Kola | Pau d'Arco |
| Chickweed | Hawthorne | Pink Root |
| Cilantro | Hops | Pipsissewa |
| Cinnamon Leaf | Horsetail | Poke Root |
| Cleaver's Herb | Hydrangea | Queen of the |
| Cola Nut | Hyssop | Meadow |
| Comfrey Leaf | Joe Pye | Redbud |
| Coriander | Johnson Grass | Red Clover |
| Croton | Juniper | Red Raspberry |
| Culver's Root | Kava Kava | Red Root |
| Damiana | Larrea | Rue |
| Dandelion | Lavender | Rumex |
| Dang Kwei | Licorice | Sacred Dock |
| Dogwood (Cornus species) | Lobelia | St. John's Wort |
| | Lomatium | Sarsaparilla Root |
| Echinacea | Marshmallow | Saw Palmetto |
| Elecampane | May Apple | Scullcap |
| False Solomon's Seal | Motherwort | Sheperd's Purse |
| Fennel | Mullein | Slippery Elm |
| Fringe Tree | Milk Thistle | Stillingia |
| Gentian | Nettle | Stone Root |
| Ginger | Oats | Sweet Leaf |
| Ginkgo | Ocotillo | Teasel |
| Thuja | Wahoo (Euonymous purpurea) | Wild Yam |
| True Solomon's Seal | | Witch Hazel |
| Tulip Poplar | Walnut | Wood Betony |
| Una de Gato | Waltheria | Wood Sorrel |
| Uva Ursi | White Oak | Yarrow |
| Valerian | Wild Violet | Yellow Dock |

EXAMPLE 17

A patient was treated in this example with a flower extract manufactured using methods described herein in example 3.

The patient presented with a cyclic, deep depression. The patient stated that everything in his life was essentially charmed including his occupation, his marriage, and children; so he was at a loss to explain the depressive episodes. Over time the mental symptoms of depression and apathy prevented successful work. The patient reported that his creativity was lost.

The inventor was the practitioner in this case. The patient was diagnosed by the practitioner with a hypothalamic-pituitary-thyroid axis disorder and prescribed a flower remedy of "Giant Arum". Applied kinesiological and other holistic pre-administration screening methods which match the appropriate remedy to the individual patient suggested that "Giant Arum" would help this case.

The "Giant Arum" essence was prepared as described in Example 3 and diluted as described in the specification. From the dosage bottle 4 drops of "Giant Arum" were given in water 2–3 times daily for six weeks, commencing in January 2000.

In follow-up visits in April 2000 and May 2000 the symptoms of depression and apathy of the patient were found to be substantially improved. He noted that his enthusiasm for work and in life returned, depressive episodes were gone.

EXAMPLE 18

An extract is manufactured as described in Examples 1 or 3 using a bloom of a plant listed in Table 1 (Example 16) and diluted as described in the specification. Approximately 4 drops of the diluted extract is added to a shampoo (16 ounces total) for the improvement of mood.

EXAMPLE 19

An extract is manufactured as described in Examples 1 or 3 using a bloom of a plant listed in Table 1 (Example 16) and diluted as described in the specification. Approximately 4 drops of the diluted extract is added to a skin cream (3 ounces total) for the improvement of mood.

EXAMPLE 20

An extract is manufactured as described in Examples 1 or 3 using a bloom of a plant listed in Table 1 (Example 16) and diluted as described in the specification. Approximately 4 drops of the diluted extract is added to a facial cosmetic (1 ounce total) to improve general vitality and to enhance the appearance of the skin.

EXAMPLE 21

Example 19 is repeated except that the extract is not diluted. Approximately ½ ounce of the undiluted extract is added to a skin conditioner (16 ounces total). Application of the skin conditioner to the skin makes the skin softer to the touch and improves vital appearance of the skin.

EXAMPLE 22

An extract of Dogwood flower is prepared as described in Example 3 and administered to a patient to allay anxiety of the patient.

Thus, although there have been described particular embodiments of the present invention of a new and useful Apparatus and Process For In Situ Manufacture of Essence From Living, Uncut Plants, it is not intended that such references be construed as limitations upon the scope of this invention except as set forth in the following claims.

What is claimed is:

1. A method for collecting an extract of a living plant, comprising:

selecting the living plant;

placing an extraction vessel proximate to a component of the living plant;

adding an amount of an extraction solution to the extraction vessel; and contacting the extraction solution to the component of the living plant for a period of time, wherein the component of the plant remains attached to the living plant during the period of time.

2. The method of claim 1, wherein the component of the living plant comprises a bloom.

3. The method of claim 1, wherein the component of the living plant comprises a bud.

4. The method of claim 1, wherein the component of the living plant is selected from a group consisting of: a leaf, a seed, a berry, and an aerial root.

5. The method of claim 1, wherein the extraction vessel is comprised of beeswax.

6. The method of claim 1, wherein the period of time comprises approximately three hours to approximately two weeks.

7. The method of claim 1, wherein the placing step further comprises passing a stem of the living plant through an opening in a wall of the extraction vessel and sealing the opening with a sealant.

8. The method of claim 7, wherein the sealant is comprised of beeswax.

9. The method of claim 8, wherein the extraction vessel is comprised of beeswax, and wherein the sealing step further comprises:

laying a strip of the sealant over the opening in the extraction vessel such that the strip of sealant covers the opening;

heating a burnishing tool;

pressing the strip of sealant and the extraction vessel together with the heated burnishing tool;

melting a sample of beeswax;

painting the melted beeswax onto the sealant, the extraction vessel, and the stem of the living plant; and allowing the sealant to cool such that a water tight seal is formed in the extraction vessel and around the stem of the living plant.

10. The method of claim 1, wherein the extraction solution comprises water.

11. The method of claim 1, wherein the collecting step further comprises the contacting step having a first period of time of approximately three hours to approximately two weeks; removing an extract; adding a second sample of extraction solution to the extraction vessel; a second contacting step having a second period of time of approximately three hours to approximately two weeks; and removing a second extract.

* * * * *